United States Patent [19]

Burleigh

[11] 4,421,719

[45] Dec. 20, 1983

[54] COLORIMETRIC INDICATORS

[75] Inventor: Malcolm B. Burleigh, St. Paul, Minn.

[73] Assignee: Minnesota Mining and Manufacturing Company, St. Paul, Minn.

[21] Appl. No.: 309,717

[22] Filed: Oct. 8, 1981

Related U.S. Application Data

[63] Continuation-in-part of Ser. No. 161,442, Jun. 20, 1980, abandoned.

[51] Int. Cl.$^3$ .................. G01N 31/08; G01N 31/22
[52] U.S. Cl. .................. 422/57; 422/87; 422/88; 422/66; 436/122; 436/131; 436/132; 436/162
[58] Field of Search ............ 23/232 R; 422/55, 56, 422/57, 58, 66, 87, 88; 436/131, 122, 134, 162

[56] References Cited

U.S. PATENT DOCUMENTS

| | | | |
|---|---|---|---|
| 3,068,073 | 11/1962 | Stanford | 23/232 R |
| 3,350,175 | 10/1967 | McConnaughey | 422/57 |
| 3,552,929 | 1/1968 | Fields et al. | 422/56 |
| 3,672,845 | 6/1972 | Verbeck | 422/57 |
| 4,326,514 | 4/1982 | Eian | 128/202.22 |

FOREIGN PATENT DOCUMENTS

| | | | |
|---|---|---|---|
| 50-970 | 1/1975 | Japan | 422/56 |
| 1574807 | 9/1980 | United Kingdom | 422/57 |

Primary Examiner—Michael S. Marcus
Attorney, Agent, or Firm—Donald M. Sell; James A. Smith; Lorraine R. Sherman

[57] ABSTRACT

A colorimetric indicator in sheet form comprising an indicator substance, a high surface area carrier for said indicator substance, and a self-adhering clay mineral binder coated on a backing is disclosed. The colorimetric indicator is useful for personal monitors, as end of service life indicators for respirators, thin layer chromatography plates, and vapor transfer sheets.

10 Claims, 5 Drawing Figures

COLORIMETRIC INDICATORS

This application is a continuation-in-part of copending application Ser. No. 161,442, filed June 20, 1980 and now abandoned.

TECHNICAL FIELD

This invention relates to colorimetric indicators useful as end of service life indicators in, for example, respirators or other passive toxic materials monitoring systems. In another aspect, this invention relates to colorimetric indicators useful in detection of fluid substances as, for example, on thin layer chromatography plates and vapor transfer sheets. Detection or monitoring is effected when the composition undergoes a visually observable reaction with the substance to be detected in the atmosphere at room temperature.

BACKGROUND ART

There is increasing interest by government agencies and the general public in protecting individuals against the harmful effects of toxic substances. In fact, personal monitoring of exposure to specific hazardous substances in the environment is required for many designated materials by government regulations. It is desirable that such devices indicate when exposure to a specific hazardous substance has reached a selected time-weighted-average value. Devices for monitoring exposure to a hazardous substance based on a visually observable change of color of a dye or color precursor incorporated therein are currently available.

Colorimetric indicators have been disclosed as useful in filtering devices, such as respirators. U.S. Pat. No. 1,537,519 discloses use of an indicator strip, such as litmus paper, in a window-type respirator. U.S. Pat. No. 4,155,358 discloses a disposable valveless chemical cartridge respirator for filtration of vinyl chloride monomer which includes a visually observable end of service life indicator. U.S. Pat. No. 4,154,586 (and related German and British Pat. Nos. 2,758,603 and 1,554,542, respectively) discloses a respirator cartridge providing a visual means for indicating organic vapor/gas hazards and incorporates a catalytic agent for enhancing activation and reaction of the indicator agent. U.S. Pat. No. 3,966,440 discloses a canister or cartridge which incorporates a colorimetric indicator for use in indicating the impending exhaustion of a toxic gas filtering device. These patents generally relate to devices with granular silica gel or alumina packed cartridges.

U.S. Pat. No. 3,350,175 relates to a finely divided non-porous inorganic carrier such as glass beads or powdered glass, the particle size being 40 to 100 mesh, on which is coated a powdered inorganic absorbent, such as clay, diatomaceous earth, or bauxite, impregnated with a colorimetric reagent. The free-flowing, discrete, coated particles of the patent are packed as an elongated bed in a transparent tube. Also relating to particles packed in a tube is U.S. Pat. No. 3,068,073 which discloses a method and reagent for detection and quantitative determination of carbon dioxide. The gas to be tested is passed through an elongated bed packed with alumina, between 16 and 200 mesh size, carrying thymol blue or thymol blue and a base.

It is known in the art to use an adhesive to secure absorptive materials to substrates. U.S. Pat. No. 3,672,845 discloses an indicator testing device wherein an indicator is incorporated in hydrophilic absorbent particulate material such as aluminum oxide, silica gel, cellulose, or vermiculite, and secured to a sheet by means of a suitable adhesive. U.S. Pat. No. 3,552,929 relates to a device for detecting halide ion concentration in fluids and discloses use of an adhesive to hold an indicator impregnated substrate, e.g., filter paper, to a backing, e.g., polyester or glass.

Heftmann, Erich, *Chromatography*, 3rd edition, Van Nostrand Reinhold Co., New York (1967), pp. 164–183, relates to thin-layer chromatography and discloses, for example, siliceous materials, cellulosics, polyamides, and dextran gels as components of coating materials for thin-layer chromatography plates.

Monitoring of personal exposure to hazardous materials is the subject of a number of studies of which the following are examples: Natusch, Sewell and Tanner, "Determination of $H_2S$ in Air—An Assessment of Impregnated Paper Tape Methods", *Analytical Chemistry*, volume 46, page 3 (1974); Schnakenberg, "A Passive Personal Sampler for Nitrogen Dioxide", *Bureau of Mines Technical Progress Report* 95 (1976); Ray, Carroll and Armstrong, "Evaluation of Small Color-Changing Carbon Monoxide Dosimeters," *Bureau of Mines Rep. Invest.* (1975); Palmer, "Personal Samplers for CO, NO and $NO_2$ in Air", *Bureau of Mines Report OFR 92-77* (1977) and Nichols, "Reactive Tapes for Automatic Environmental Analysis, Personal Vapor Monitoring Badges for Industrial Workers", *National Science Foundation Report NSF/RA-780039* (1978).

Indicators in sheet form have been utilized in the prior art. The method of coating the carrier and dye material onto a film backing employs binders of soluble organic polymers or organic polymers dispersed in an aqueous phase. These organic polymer binding systems suffer serious drawbacks and limitations. In order to bind the carrier particles so that they will adhere, it is necessary to coat the particles themselves with resin. This coating lowers the ability of the carrier particles to adsorb the dye. In addition, the hazardous gas must penetrate a layer of resin polymer in order to reach the adsorbed dye. This coating also serves to slow the rate of reaction. Thus, resin binders tend to create exactly the opposite effect than intended.

In addition to the above limitations, there is the interaction of certain reactants with organic compounds. Chemicals such as permanganate salts, chromate salts, strong acids and bases and other reactive materials useful in dye and dye precursor formulations are often not stable in contact with organic materials and thus cannot be used with organic resin binders.

The colorimetric indicators of the present invention overcome the above-mentioned limitations of the organic resin binders included in the prior art compositions. The present invention provides colorimetric indicators comprising certain clay mineral binders, which clays possess properties of high porosity, large specific surface area, superior adhesiveness, stability towards many dyes and dye precursors, ready availability and economy.

Clays have been used for numerous purposes, many of which depend on their adsorptive ability. They have been used as sweeping compounds, as drilling muds in oil drilling, and in ceramics. There are many references to their use as dye acceptors or pigmented particles. See, for example, R. W. Grimshaw, *The Chemistry and Physics of Clay*, Wiley-Interscience, London (1971) pp. 120–124, 140–148.

DISCLOSURE OF INVENTION

The colormetric indicators of the present invention are sheet materials comprising an indicator substance coated on a backing. The indicator substance may be a color precursor, a dye or a bleachable dye which will form a different color when a selected substance reacts directly with the indicator or the indicator reacts with products of a previous reaction. The colorimetric indicator comprises an indicator substance, a carrier, and a clay mineral binder coated on a backing. In some instances, the clay mineral is used as the binder and also as the high surface area carrier. In other instances, a high surface area carrier such as alumina, carbon or silica is used.

The present invention utilizes self-adhering clay mineral binders which may be used in some cases without additional adsorbent carrier materials in the formation of colorimetric indicators. In such cases the carrier and the clay mineral are one and the same substance. The clay binder acts as an adsorbent as well as causing the coating to adhere to the film backing. The resultant coatings are more economical than resin bound coatings although they tend to scratch, mar and rub off. However, for their intended uses as, for example, an indicator in a controlled sensitivity monitoring device such as disclosed in U.S. Pat. No. 4,158,958, it is not necessary to have a very strong coating. Superior adhesion may be sacrificed for improved sensitivity and selectivity.

When a carrier other than the clay mineral is present it may be alumina, silica, carbon or other similar high surface area material which acts as a medium for toxic substance adsorbance. In all cases, the indicator substances and the toxic substances to be detected by the indicator coatings must be adsorbed onto the carrier. The clay binder is self-adhering and requires no supplementary adhesive. The clay binder is the cement that holds the carrier particles together and also holds the coating to the backing. The colorimetric indicators of the present invention are useful where porosity and large specific surface area are important, as in toxic gas detection, thin layer chromatography plates and vapor transfer sheets.

DETAILED DESCRIPTION OF THE INVENTION

The present invention provides a colorimetric indicator in sheet form for the detection of a hazardous or other substance in ambient air comprising a backing on which is coated a colorimetric indicator comprising
a. an indicator substance,
b. a high surface area carrier for said indicator substance, and
c. a self-adhering clay mineral binder,
said clay mineral being said binder or both said binder and said carrier, which colorimetric indicator is reactive with said hazardous or other substance, said colorimetric indicator upon exposure to said substance undergoing an irreversible chemical reaction which progresses, as a function of diffusion, through the depth of the coating, resulting in a visually resolvable color change. The rate of the chemical reaction is proportional to the amount of indicator substance present and the concentration of the substance to be monitored, the color change indicating that exposure to said hazardous substance has reached a selected time-weighted-average value. The colorimetric indicator is a porous coating upon a backing permitting gaseous diffusion of the hazardous or other substance thereinto.

Figure 1:
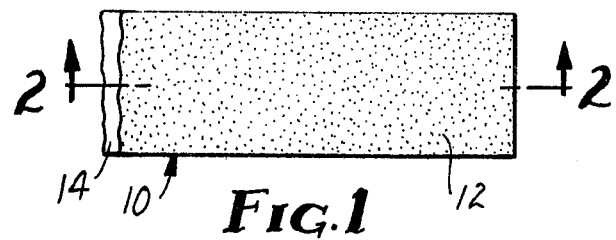
FIG. 1 is a top plan view of a colorimetric indicator of the present invention.
Figure 2:
FIG. 2 is a sectional view of the colorimetric indicator material of FIG. 1 taken along the line 2—2.

Referring to the accompanying drawing, the colorimetric indicator 10 of the present invention comprises an indicator substance 12 coated on a backing 14, as shown in FIGS. 1 and 2.

The colorimetric indicator of the present invention comprises an indicator substance which may be a dye precursor or a dye or bleachable dye, a clay mineral binder, and an adsorbent carrier which may be the clay mineral. The carrier adsorbs the indicator substance as well as the toxic substances to be monitored. Among useful carriers other than clay are alumina, silica, carbon, and similar highly porous materials. Among the useful indicator substances are dyes such as permanganate salts, chromate salts, indophenol sodium salt, and other water soluble dyes such as uranine (sodium salt of fluorescein) and the sodium salt of the leuco sulfuric derivative of Vat Green 1. It is anticipated that any dye which does not adversely react with the carrier and binder materials will be useful. These dyes may be used singly or in combination in order to achieve the desired imaging properties.

The use of the colorimetric indicator for a particular contaminant is dependent on the selection of an appropriate indicator substance. For example, carbon monoxide can be detected by its reaction with pink silver permanganate to form the beige composition, $MnO_2$ and other reaction products.

The novel binders of the present invention are self-adhering inorganic minerals, namely clays, which are capable of holding the particles together and also of bonding the coating to the film backing.

Two general classes of clay minerals useful in the present invention are attapulgus clays and the smectite or bentonite clays. In the case of the bentonite clays, their binding action is so good that it is possible to put many more times its weight of other substances such as silica gel, alumina or any adsorbent materials one would wish into the formulation. The attapulgus clay is preferably used by itself due to its less efficient binding action.

Attapulgus clay is a fibrous clay related to the asbestos minerals. Two names, palygorskite and attapulgite, have been applied to the same mineral. It is composed of magnesium silicate chains which have been partially replaced with aluminum, calcium and iron. A hypothetical chemical formula (disregarding the above mentioned impurities) would be $(Si_2O_5)_4{}^{8-}(Mg_5(OH)_2)^{8+}(OH_2)_4 \cdot 4H_2O$.

The bentonite clays are represented by a number of clay minerals of varying composition. They all have a similar overall structure and thus have similar physical properties. These bentonite clays have, in common, a double tetrahedral layer sandwiching two or three octahedral layers. The general structure of the bentonite clays is complicated by substitution of other metal ions with similar structural parameters for the aluminum and silicon normally in the various layers. Some sample bentonite clays and their formulas are shown in TABLE I below. The common names of these clays are smectites, montmorillonites or bentonites. They will be referred to herein as bentonites except where the reference is to a specific mineral. For a more complete description of these materials see Grimshaw, supra.

TABLE I
COMPOSITIONS OF SAMPLE BENTONITE CLAYS

| Name | Composition of Octahedral Layers | Composition of Tetrahedral Layers | Number of Octahedral Layers |
|---|---|---|---|
| Wyoming Bentonite | $(Al_{1.53}Fe_{.18}^{3+}Mg_{0.33})$ | $[(Al_{0.13}Si_{3.87})O_{10}(OH)_2]Na_{.33}$ | 2 |
| Beidellite | $(Al_{1.46}Fe_{.50}^{+}Mg_{.08})$ | $[(Al_{.36}Si_{3.64})O_{10}(OH)_2]Na_{.40}$ | 2 |
| Montmorillonite | $(Al_{1.51}Fe_{.07}^{3+}Mg_{.33})$ | $[(Al_{0.13}Si_{3.87})O_{10}(OH)_2]Na_{.33}$ | 2 |
| Nontronite | $(Fe_{1.67}^{3+}Mg_{0.33}^{+2})$ | $[Si_4O_{10}(OH)_2]Na_{.33}$ | 3 |
| Hectorite | $(Mg_{2.67}Li_{.33})$ | $[S_4O_{10}(F,OH)_2]Na_{.33}$ | 3 |
| Saponite | $Mg_3(Al_{.33}Si_{3.67})$ | $[O_{10}(OH)_2]Na_{.33}$ | 3 |

Bentonites exhibit, when wet, great plasticity, stickiness, and strength. These properties are believed due to two factors: the platelet nature of the particles and the extremely large specific surface area. The adsorptive property of bentonites is of great importance in the present invention. Bentonites possess the ability to adsorb strongly many organic molecules as well as inorganic molecules. Bentonites as binders are preferred in the colorimetric indicators of this invention.

Attapulgus clays possess good adsorptive properties, but as mentioned above, they have less binding ability than bentonite clays.

Clay binders are particularly well suited for inclusion in toxic gas detectors due to their adhesion to commonly used backing materials. Clays, because of their structure, have natural adhesive properties and no supplementary adhesive is used in the practice of the present invention to adhere the indicator coating to the backing. It is indeed surprising that adhesive forces between clay particles and between clay particles and backing materials exist that enable one to successfully prepare sheet materials. Clay binders are well-suited for use in toxic gas detectors due to their outstanding porosity and their inertness towards commonly used dyes and dye precursors. Backing materials which are transparent, translucent or opaque have been found useful in the present invention. If the indicator is on an opaque or translucent backing, the color comparison is made on the side exposed to the hazardous material. If the indicator is on a transparent backing, it is then possible to make the comparison from either side. However, since the colorimetric indicators are in sheet form, contamination of the indicator coating by reaction with the backing must be avoided. An additional prerequisite is that the backing must be wettable by the coating solution. Glass has been found to work well and polyester or other flexible films may be useful if properly surface-treated to make them water wettable. Polyester is relatively impermeable; thus, its organic constituent components will not normally react with the indicator. Many types of surface treatments will render plastic films water wettable. High voltage corona discharge treatment is useful in making polyester films water receptive and since it does not involve the use of chemicals there is no possibility of contamination of the subsequently applied indicator coating.

Colorimetric indicators, coated on flexible backings to form sheet materials, are useful for monitoring toxic substances in passive mode services and in respirators. These flexible sheet materials must be capable of being cut. Colorimetric indicators coated on non-flexible backings such as glass are useful, for example, as thin layer chromatography plates. In addition, indicator coatings of the present invention must resist loss of adhesion, often referred to as "peeling," and loss of cohesion or "rubbing off". Both of these failures can be related to the following variables: nature of the indicator substances, the carrier to binder ratio, and the coating weight.

The coating weight refers to the total loading in grams per square meter. A high coating weight affords maximum exposure of toxic substances to the porous coating surface which holds a maximum amount of indicator substance. However, a high coating weight tends to make the coating susceptible to cracking and then peeling. Hence, there is a practical limit to the coating weight. As the carrier to binder ratio increases, the binding forces lessen, and the coating becomes increasingly soft and chalky and subject to rubbing off. This consideration places an upper limit on the carrier to binder ratio. Thus, excessive coating thickness may result in peeling whereas an excessively high carrier content may result in rubbing off of the coating. To evaluate carrier to binder ratio, the followng test was devised.

SAND DROP TEST FOR CLAY COAT

A modified ASTM method was used to test the strength of clay coated films. Several films were prepared by coating various preparations of ball milled RA-1 alumina (activated alumina, Reynolds Corp.) and USP bentonite. An alumina slush grind was prepared using 100 g of the Reynolds activated alumina, 200 g water and 300 g of 1.3 cm glass grinding balls which were placed in a ½ liter jar and milled for 36 hours on a roller mill.

20 g USP bentonite clay was added to 180 g water in a ½ liter jar and dispersed on a high speed mixer. All the solutions were prepared to 15% total solids and doctor blade coated on corona treated 50 polyester backing. The nominal coating weight was 28 g/m². The following alumina/bentonite ratios were tested: 5/1, 10/1, 15/1, 20/1, 30/1. The integrity of the coatings was tested by dropping 30 g of sand (mesh size 0.290 mm×0.053 mm) through a distance of 0.3 meter (1 ft) onto the sheet taped onto a glass plate inclined at a 30° angle.

The results of the test are given in TABLE 2:

TABLE 2

| Sand Drop Test for Clay Coated Films | |
|---|---|
| Alumina/bentonite ratio | Result |
| 5/1 | slight abrasion |
| 10/1 | slight abrasion |
| 15/1 | slight abrasion |
| 20/1 | slight abrasion with small pinholes |
| 30/1 | small hole |

TABLE 2-continued

| Sand Drop Test for Clay Coated Films | |
|---|---|
| Alumina/bentonite ratio | Result |
| pure Al₂O₃ coating | severely abraded |

The data indicate that 20/1 is the maximum useful alumina/bentonite ratio.

The colorimetric indicators of the present invention, in sheet form, find use as indicators for toxic substances in passive mode devices. The use of these materials as end of service life indicators in cartridge respirators is the subject of assignee's copending application, now U.S. Pat. No. 4,326,514, filed June 20, 1980.

EXAMPLE 1

(a) 100 g Reynolds RA-1 activated alumina (Reynolds Corp.), 200 g water, and 300 g of 1.3 cm glass grinding balls were added to a ½ liter jar and milled for 35 hours on a roller mill. 240 g of this alumina slush grind, 20 g USP bentonite clay, 1 g silver nitrate, 1 g potassium permanganate and 400 g of water were added to a liter jar and dispersed with a high speed mixer. The dispersion was a uniform pink color. The dispersion was coated on 50 polyester backing which had been primed using a high voltage corona so that the backing was water wettable. The film was coated 100 wet and the eventual dry coating weight was 25 g/m². The drying was done using a 14 amp hot air heat gun.

Figure 3:
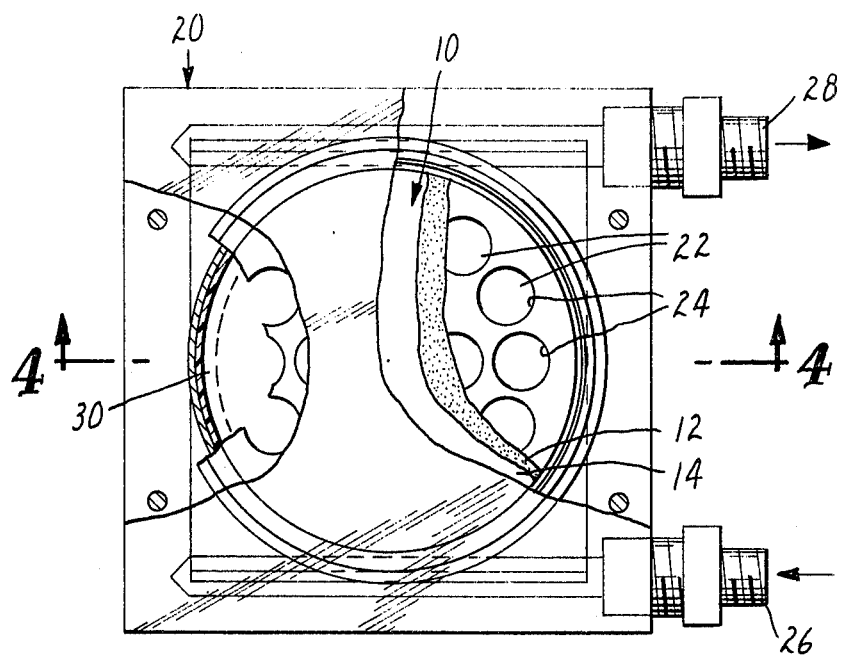
FIG. 3 is a top plan view, with parts thereof broken away, of a diffusional gas monitoring device.
Figure 4:
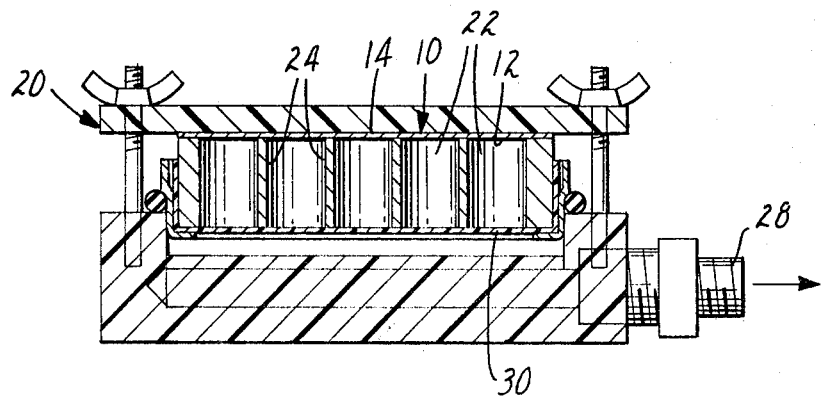
FIG. 4 is a sectional view of the diffusional gas monitoring device of FIG. 3 taken along line 4—4.

(b) Referring now to FIGS. 3 and 4 of the drawings, samples of the sheet form colorimetric indicator were exposed to the toxic gas CO in diffusional monitoring device 20. Assignee's U.S. Pat. No. 4,158,958 is directed to such devices. Diffusional monitoring device 20 had nineteen apertures 22, each with straight walls 24, a diameter of 1 cm and a height of 1.2 cm. Gas inlet 26 and outlet 28 allowed a 10 liters/min airstream containing 20 ppm CO to pass through device 20, diffuse through porous film 30 (Celgard 2400, Celanese Plastics Company), the purpose of which was to assure sampling by diffusion rather than direct air flow, into passive air space of aperture 22, and contact colorimetric indicator coating 12 which is on backing 14 and exit through outlet 28. The sample colorimetric indicators were removed at various times and the reflectance density was measured. The initial color density was 0.54 log density units measured using a MacBeth 514 reflecting densitometer with a green filter. After exposure to carbon monoxide the density of the completely reacted indicator substance was 0.37 log density units. The decrease in density coincided with the indicator color change from pink to beige, indicating the ability of the device to accurately measure the amount of CO gas present.

The experimental resuts are listed in TABLE 3.

TABLE 3

| Time-Reflectance Density Data | |
|---|---|
| Minutes | Ref. Density |
| 0 | 0.54 |
| 1 | 0.51 |
| 3 | 0.47 |
| 5 | 0.45 |
| 10 | 0.39 |
| 60 (complete reaction) | 0.37 |

The data indicate a smooth decrease in the reflectance density corresponding to the time of exposure to the CO airstream. The final data corresponds to the lower limit of reflectance density, a complete reaction.

The colorimetric indicator as formulated herein is extremely sensitive to carbon monoxide. In order to operate a useful device containing this colorimetric indicator, a sufficient degree of attenuation must be realized. That is, in using device 20 of FIGS. 3 and 4, the size of the diffusion apertures 22 needs to be reduced to accommodate the extreme sensitivity of the indicator and the relatively large time-weighted average CO value of 400 ppm-hrs.

Figure 5:
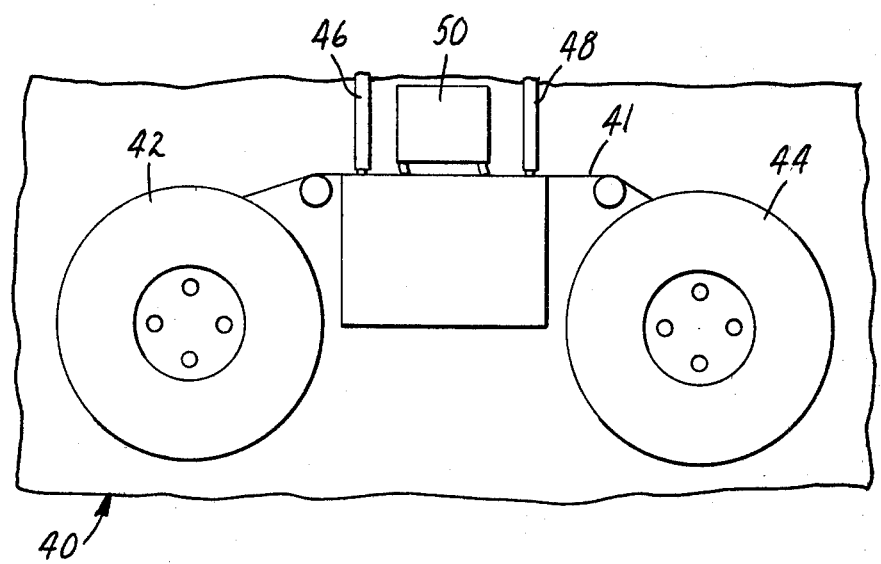
FIG. 5 is a partial elevational view of a continuous-type gas monitoring device.

Referring now to FIG. 5, a continuous-type CO monitor 40 utilizing the colorimetric indicator of this invention is shown. The indicator tape 41 was unwound from spool 42 onto take-up spool 44 and passed under optical fore sensor 46, optical aft sensor 48, and exposure chamber 50 into which air was pumped at a specific rate.

The two sensors measured the amount of light reflected by the tape as a voltage. When the CO reacted with the colorimetric indicator tape, its color changed from pink to beige, which the sensor saw as an increase in the reflected light. Initial color density was 0.54 log density units using a MacBeth 514 reflecting densitometer. A green filter was used after exposure and the density of the beige material was 0.37 log density units after complete reaction with CO gas. The decrease in reflective density coincided with the indicator color change from pink to beige. The voltage difference between the fore and aft sensors was then proportional to the CO concentration in the stream. When the voltage difference exceeded a preset level, a relay was tripped and an alarm was activated.

EXAMPLE 2

40 g high surface area silica gel, 20 g USP bentonite, 4 g chromium trioxide, 10 g sulfuric acid and 200 g water were dispersed in a ½ liter jar by ball milling with 300 g of 1 cm balls for 1 hour. The dispersion was a bright yellow and was coated 100 wet on corona primed polyester and dried using the procedure of EXAMPLE 1.

The coated film was exposed to air containing 950 ppm isopropanol at 50% relative humidity at 25° C.

The coated film was mounted into the diffusional monitoring device of FIGS. 3 and 4, said device having straight walls, a diameter of 1 cm and a height of 1.2 cm.

The optical density was measured through the back of the film using a Macbeth 514 Reflectance Densitometer set with a blue filter and initially was found to be 0.46 log density units. After being exposed for 22.5 minutes, the density had decayed to a stable value of 0.09.

The visual color change was from yellow to light green and this was quantified by the optical density measurements, thus indicating the presence of isopropanol vapors.

EXAMPLE 3

33 g attagel (attapulgite clay) was added to 200 g water, 333 mg sodium salt of indophenol and 1.5 g sodium hydroxide. The mixture was dispersed in a ½ liter jar with 300 g of 1 cm balls by ball milling for 1 hour. The dispersion was coated and dried using the process of EXAMPLE 1.

The colorimetric indicator was exposed to air containing 500 ppm SO₂ at 50% relative humidity at 25° C. in the diffusional monitoring device of FIG. 3. The optical density was measured through the back of the film using a Macbeth 514 Reflectance Densitometer set with a yellow filter. The optical density was initially 0.57 log density units. After 7.2 minutes, the optical density had decayed to a stable value of 0.10. The visual color change was from blue to white, the color change being quantified by the optical density measurements, thus indicating the ability of this device to accurately measure the amount of $SO_2$ gas present.

What is claimed is:

1. A colorimetric indicator in sheet form for the monitoring of a hazardous substance in ambient air comprising a flexible, non-adhesive bearing, organic film backing on wich is coated a colorimetric indicator consisting essentially of
   a. an indicator substance selected from permanganate salts,
   b. a high surface area carrier for said indicator substance selected from the group consisting of alumina and silica, and
   c. a self-adhering bentonite clay mineral binder,
   said colorimetric indicator upon exposure to said hazardous substance undergoing an irreversible chemical reaction which progresses, as a function of diffusion, through the depth of the colorimetric indicator resulting in a visually resolvable color change, the rate of said reaction being proportional to the amount of said indicator substance present and the concentration of said hazardous substance to be monitored, said color change indicating that exposure to said hazardous substance has reached a selected time-weighted-average value.

2. The colorimetric indicator according to claim 1 wherein the high surface area carrier is silica.

3. The colorimetric indicator according to claim 1 wherein the high surface area carrier is alumina.

4. The colorimetric indicator according to claim 1 wherein the backing is a transparent polyester film.

5. A colorimetric indicator in sheet form for the detection of fluid substances comprising a flexible, non-adhesive-bearing, organic film backing on which is coated a colorimetric indicator consisting essentially of
   a. an indicator substance selected from permanganate salts,
   b. a high surface area carrier for said indicator substance selected from the group consisting of alumina and silica, and
   c. a self-adhering bentonite clay mineral binder,
   said colorimetric indicator upon exposure to said fluid substance to be detected undergoing an irreversible chemical reaction which progresses, as a function of diffusion, through the depth of the colorimetric indicator resulting in a visually resolvable color change, the rate of said change being proportional to the amount of said indicator substance present and the concentration of said fluid substance to be detected.

6. The colorimetric indicator according to claim 5 wherein the carrier is silica.

7. The colorimetric indicator according to claim 5 wherein the carrier is alumina.

8. The colorimetric indicator according to claim 5 wherein the backing is a transparent polyester film.

9. A thin layer chromatography plate comprising a colorimetric indicator coated on a flexible, non-adhesive-bearing, organic film backing, said colorimetric indicator consisting essentially of
   a. an indicator substance selected from permanganate salts,
   b. a high surface area carrier for said indicator substance selected from the group consisting of alumina and silica, and
   c. a self-adhering bentonite clay mineral binder.

10. A vapor transfer sheet comprising a colorimetric indicator coated on a flexible, non-adhesive-bearing, organic film backing, said colorimetric indicator consisting essentially of
    a. an indicator substance selected from permanganate salts,
    b. a high surface area carrier for said indicator substance selected from the group consisting of alumina and silica, and
    c. a self-adhering bentonite clay mineral binder.

* * * * *

UNITED STATES PATENT AND TRADEMARK OFFICE
CERTIFICATE OF CORRECTION

PATENT NO. : 4,421,719

DATED : December 20, 1983

INVENTOR(S) : Malcolm B. Burleigh

It is certified that error appears in the above-identified patent and that said Letters Patent is hereby corrected as shown below:

Column 10, lines 21 to 30, Claim 9, delete entire claim.

Signed and Sealed this

Eighteenth Day of March 1986

[SEAL]

Attest:

DONALD J. QUIGG

Attesting Officer     Commissioner of Patents and Trademarks